United States Patent [19]

Green

[11] Patent Number: 4,806,526

[45] Date of Patent: Feb. 21, 1989

[54] ANTIALLERGENIC AGENT

[75] Inventor: Wesley F. Green, Valley Heights, Australia

[73] Assignee: University of Sydney, Sydney, Australia

[21] Appl. No.: 921,911

[22] Filed: Oct. 22, 1986

Related U.S. Application Data

[63] Continuation of Ser. No. 753,215, Jul. 9, 1985, abandoned.

[30] Foreign Application Priority Data

Jul. 11, 1984 [AU] Australia ............................. PG5962

[51] Int. Cl.$^4$ ............................................. A01N 43/04
[52] U.S. Cl. ................................................... 514/23
[58] Field of Search ............................ 514/533, 730, 23

[56] References Cited

U.S. PATENT DOCUMENTS 1,514,377 11/1924 Dow et al. ........................ 514/730
3,996,380 12/1976 Henrick ............................. 514/533
4,666,940 5/1987 Bischoff et al. ................... 514/533

FOREIGN PATENT DOCUMENTS 501752 4/1954 Canada ............................... 514/533
7128797 8/1971 Japan ................................. 514/730

OTHER PUBLICATIONS

The Merck Index 10th ed. 1983, Ref. nos. 3132 and 8928.
Chemical Abstracts 101:149601h (1984).

Primary Examiner—Leonard Schenkman
Attorney, Agent, or Firm—Sprung Horn Kramer & Woods

[57] ABSTRACT

House dust mite allergens and plant allergens are removed by treatment with tannic acid solution. A miticide may be included to kill dust mites. A preferred miticidal antiallergenic agent comprises benzyl alcohol, ethanol, tannic acid and water.

12 Claims, No Drawings

ANTIALLERGENIC AGENT

This is a continuation of application Ser. No. 753,215, filed 7-9-85, now abandoned.

FIELD OF THE INVENTION

The present invention relates to the use of tannic acid to remove allergens from an environment.

PRIOR ART

Diseases thought to have an "allergic" basis such as asthma, hay fever, eczema and urticaria have plagued man for a long time. In the past few decades it has become clear that house dust mites are extremely allergenic and there is now evidence that continued avoidance of contact with these allergens may result in a decrease of bronchial hyperreactivity in mite sensitive asthmatics. Attempts have been made to prevent contact with allergens by employing air filters, special vacuum cleaners, mattress covers etc., but so far the results have been disappointing.

The house dust mite *D. farinae* and *D. Pteronyssinus* can live in blankets, sheep skins and probably in any place where human skin scales or other mite fodder can accumulate, including house dust. Simply killing the mites in these places does not necessarily reduce the allergens in the environment because dead mites remain allergenic and can slowly release more allergen as they break down. It is obvious that an agent which could destroy the allergenic material in dusts, blankets and bedding, would be of great value.

During a preliminary investigation into the chemical nature of mite allergens it was observed that common oxidising or reducing agents, divalent and trivalent cations, alkalis, aldehydes and mild acids had no effect on the allergenicity of house dust mite allergens. Other workers have reported that the allergens have the ability to withstand even proteolytic digestion. Thus the allergens appear to be very stable and this no doubt contributes to their persistence in the environment.

AIM OF THE INVENTION

The invention aims to provide an effective antiallergenic agent.

SUMMARY OF THE INVENTION

The present invention provides a method of removing allergens from an environment, which comprises treating the environment with tannic acid.

The invention also provides an antiallergenic composition which comprises tannic acid and a carrier.

Generally, the composition comprises 0.1–10 wt% tannic acid; preferably about 1 wt%.

The composition may be in the form of a liquid, spray, aerosol, or any other convenient form. An aqueous solution is generally preferred.

Alternatively, the air in the environment may be passed through a tannic acid treatment screen to remove allergens, e.g. by bubbling the air through a tannic acid solution. A suitable device for treating the air may be incorporated in a conventional air conditioning system.

The composition might be used to wash allergen—contaminated walls, floors, clothing, bedding pillows, curtains, floor coverings or any other washable parts of the environment.

Tannic acid has been shown to have no substantial discolouring effects on light coloured carpets and fabrics. Any slight discolouration could be easily removed by rinsing in water.

It is preferred to treat the area with an insecticide (i.e. miticide) to kill living mites, before applying the tannic acid to reduce the allergenicity of the mite debris. Conventional insecticides such as pyrethrins, pyrethroids or organophosphorus compounds may be used. However, alcohols such as ethanol and benzyl alcohol have been found to be particularly effective as miticides. A composition comprising at least 10 vol% benzyl alcohol has been found to be especially good. A surfactant may be included also.

A preferred miticidal composition comprises a 0.5 to 5% w/v solution of tannic acid in a solvent comprising:
ethanol 0.20–40% v/v
water 0.50–70% v/v
benzyl alcohol 0.5–20% v/v Tannic acid applied as a 1 wt% aerosol was found to be non-irritating to the human upper respiratory mucosa or lungs.

Treatment with tannic acid has been found to substantially reduce most allergens. House dust allergens and some plant allergens may be almost completely removed. Food allergens may also be treated.

Procedures for chemically altering protein material have been known for centuries. The tanning of animal hides to make leather is an example, and recently artificial horn and tortoiseshell have been made by treating gelatin and albumin with tannic acid. Tannic acid has been used to alter chemically the molecular surface on cell membranes to permit the bonding of antibodies in agglutination assays. The tanning process in general involves the introduction of polymerising phenol groups and a reduction in protein bound water. As a result the protein becomes insoluble and more hydrophobic.

DESCRIPTION OF EXPERIMENTAL WORK

The invention will now be further described by way of example only.

I. TREATMENT WITH TANNIC ACID SOLUTION

Experiment 1.

Effect of tannic acid on house dust allergen

Two 0.42 g samples of house dust which contained 2666 *Dermatophagoides pteronyssinus* mites per gram were placed in tubes A and B. Seven ml of distilled water were added to A and 7 ml of 1% aqueous tannic acid solution were added to B. The samples were shaken for 3 minutes and let stand for two hours, after which the supernates from both samples were used to skin test a subject known to give positive skin reactions to house dust mites. Distilled water was used as a negative skin test control. All test were repeated six times.

Experiment 2

Dialysis of tannic acid treated house dust

Samples A and B from Experiment 1, i.e. dust extracts with and without tannic acid and containing suspended dust material were dialysed against cold distilled water for 72 hours to remove tannic acid, and the skin tests using these samples were repeated.

Experiment 3

Some D. pteronyssinus extract was treated separately with 1% and 2% tannic acid in 0.25% aqueous solution of a common laundry detergent and tested for skin reaction. D. pteronyssinus extract plus detergent was used as a positive control.

Experiment 4

Effect of detergent on allergens previously treated with tannic acid

A dust sample that had had its allergens removed by 1% tannic acid was treated with 0.25% laundry detergent and skin tests again performed.

Experiment 5

Plant allergens and tannic acid

Commercial extracts of the grass *Phleum pratense* and the weed *Plantago lanceolata* were dialysed until free from glycerol and treated with 1% tannic acid and skin tests performed as before.

Results

The results of the skin tests are shown in Table I.

TABLE I

| Test No. | Skin Tests (weal diameter mm) | | |
|---|---|---|---|
| | Experiment 1 | | |
| | House dust plus water (sample A) | House dust plus 1% tannic acid (Sample B) | Distilled water (control) |
| 1 | +ve | −ve | −ve |
| 2 | + | − | − |
| 3 | +all | − | − |
| 4 | +5 × 5 | − | − |
| 5 | + | − | − |
| 6 | + | − | − |
| | Experiment 2 | | |
| | Dialysed house dust plus water | Dialysed house dust plus tannic acid | |
| 1 | +ve | −ve | |
| 2 | + | − | |
| 3 | +all | − | |
| 4 | +5 × 5 | − | |
| 5 | + | − | |
| 6 | + | − | |
| | Experiment 3 | | |
| | House dust mite (*D. pteronyssinus*) plus detergent plus | | House dust mite (*D. pteronyssinus*) plus detergent only |
| | 1% tannic acid | 2% tannic acid | |
| 1 | + | −ve | + |
| 2 | +all | 2 × 2 | + |
| 3 | +5 × 5 | − | +all |
| 4 | + | − | +6 × 6 |
| 5 | + | 3 × 3 | + |
| 6 | + | 2 × 2 | + |
| | Experiment 4 | | |
| | Tannic acid treated house dust + detergent | | |
| 1 | −ve | | |
| 2 | − | | |
| 3 | − | | |
| 4 | − | | |
| 5 | − | | |
| 6 | − | | |
| | Experiment 5 | | | |
| | Timothy grass (phlem) extract | Timothy grass +1% tannic acid | Plantago extract | Plantago +1% tannic acid |
| 1 | +ve | −ve | +ve | −ve |

TABLE I-continued

| Test No. | Skin Tests (weal diameter mm) | | | |
|---|---|---|---|---|
| 2 | + | − | + | − |
| 3 | +all | − | +all | − |
| 4 | +9 × 7 | − | +7 × 6 | − |
| 5 | + | − | + | − |
| 6 | + | − | + | − |

The results show that 1% tannic acid solution completely abolishes the allergenicity of house dust and the dust does not regain its allergenicity when the tannic acid is dialysed out. If tannic acid is combined with an alkaline laundry detergent it is only moderately effective in removing the allergens but dust which has had its allergens removed by tannic acid treatment remains free of allergen when subsequently exposed to detergent.

The plant extracts of Phleum and Plantago also lose their allergenicity when treated with tannic acid.

Clearly tannic acid is able to abolish allergens in house dust and some plants, and plausibly may be effective against many more allergens. Washing articles of clothing, bedding, pillows, drapes etc. in 1% tannic acid solution may prove to be an effective way of reducing environmental allergens. This could be particularly useful in poorer communities where it is often uneconomical to destroy materials which are heavily contaminated with house dust mites.

II. TANNIC ACID—MITICIDE COMPOSITION (A) A solution has now been prepared which in the laboratory effectively kills the house dust mites *Dermatophagordes pteronyssinus* and *Dermatophagoides farinae* and also removes the allergens associated with the mites, such as those from mite body fragments or mite faeces. Studies indicate that other allergens present may also be inactivated.

The mite killing compound which has been incorporated into the 1% aqueous tannic acid solution is benzyl alcohol, a non toxic, low volatile alcohol (boiling point 203°–208° C.) used in the perfume and food flavouring industry. Benzyl alcohol was found to be most effective in killing mites when it was used as a 10% solution or higher concentration. To enable this amount of benzyl alcohol to dissolve in the aqueous tannic acid solution it has been necessary to add 30% ethyl alcohol as a solvent. The resultant composition is:

Ethyl Alcohol 30% v/v
Water 60% v/v
Benzyl Alcohol 10% v/v
Tannic Acid 1% w/v in the above mixture The solution of this composition has unique properties which enhance its use as a miticide in household carpets etc. Namely, when the solution is applied to a surface or fabric the initial concentration of benzyl alcohol is 10% v/v. On exposure to air the ethyl alcohol component is rapidly lost by evaporation. This results in the benzyl alcohol coming out of solution in the form of small well dispersed droplets which can be readily observed under a microscope. This takes place because an aqueous solution with no ethyl alcohol in it can only hold about 4 vol % benzyl alcohol. The net effect is that as the ethyl alcohol evaporates, local high concentrations of benzyl alcohol can occur in carpet fibres etc, with consequent enhancement of its miticidal properties. The allergen destroying properties of the tannic acid remain unaltered.

(B) Table II shows the effect of the tannic acid—ethyl alcohol—benzyl alcohol—water mixture on living Dermatophagoides mites, as compared with some other substances tested.

TABLE II

| NO. | SUBSTANCE TESTED | SURVIVAL TIME OF MITES | |
|---|---|---|---|
| | | D. pteronyssinus | D. farinae |
| 1 | KEROSENE | >4 hrs | >4 hrs |
| 2 | INSECTICIDE (1)<br>Tetramethrin 0.27%<br>Phenothrin 0.95%<br>Piperonyl butoxide 1.08% | 17 min | 34 min |
| 3 | INSECTICIDE (2)<br>Tetramethrin 0.36%<br>Phenothrin 0.1%<br>Allethrin 2.8% | >1 hr | >1 hr |
| 4 | SURGICAL ANTISEPTIC<br>Iodine 1% +<br>Surfactant | >4 hrs | >4 hrs |
| 5 | ETHYL ALCOHOL | 11 min | 45 min |
| 6 | ETHYLENE GLYCOL | >4 hrs | >4 hrs |
| 7 | SPRAY DISINFECTANT<br>N.alkyl dimethyl benzyl-<br>ammonium chlorides 0.1%<br>Triethylene glycol 8%<br>Ethanol 37% | 11 min | 36 min |
| 8 | METHYL BENZOATE<br>(a veterinary miticide) | 45 min | >45 min |
| 9 | BENZYL ALCOHOL (NEAT) | 1 min | 2 min |
| 10 | BENZYL ALCOHOL-TANNIN-WATER<br>("antiallergenic agent") | 2-3 min | 5 min |

Mites of both species proved to be extraordinarily hardy and were often observed living entirely submerged by some test solutions (not given above) 24 hours after beginning the experiment.

(C) Because of its potency in killing mites, its low toxicity, faint pleasant odour and low vapour pressure (<1 mm Hg at 20° C.) benzyl alcohol was chosen as a suitable mite killing additive to the original aqueous tannic acid solution. Table III shows survival rates of the mites D. pteronyssinus and D. farinae when exposed to tannic acid—water—alcohol—benzyl alcohol mixture on a welled glass slide.

TABLE III

| EXPERI-<br>MENT<br>NUMBER | SURVIVAL RATES OF DERMATOPHAGOIDES Spp. IN CONTACT WITH "ANTIALLERGINIC AGENT" | |
|---|---|---|
| | D. pteronyssinus<br>minutes/seconds | D. farinae<br>minutes/seconds |
| 1 | 2  52 | 7  32 |
| 2 | 3  26 | 7  43 |
| 3 | 4  00 | 6  30 |
| 4 | 3  35 | 7  08 |
| 5 | 3  00 | 7  35 |
| 6 | 3  00 | 9  00 |
| 7 | 3  35 | 9  32 |
| 8 | 3  58 | 10  01 |
| 9 | 4  26 | 8  52 |
| 10 | 3  43 | 7  00 |
| | N = 10<br>MEAN = 3 mins 33 secs<br>SD  30 secs | N = 10<br>MEAN = 8 mins 5 secs<br>SD  1 min 19 secs |

D. farinae was the hardier of the two mites but both mites were quickly killed by the antiallergenic agent. The above experiments also showed that benzyl alcohol retains its miticidal properties when mixed with the other components of the solution. In consequence, a mixture of benzyl alcohol-tannic acid-ethyl alcohol and water in the proportions described above both kills mites and destroys their allergenicity. Such an agent has wide potential application in the control of environmental allergens and could be of great benefit to sufferers of allergic diseases and asthma.

III POSSIBLE ADVERSE EFFECTS

Possible adverse effects of the solution when inhaled were sought in normal and asthmatic patients. Four moderately severe to severe asthmatics and 2 normals have been bronchially challenged with increasing aerosolised doses of the antiallergenic agent. The doses, delivered via aerosol spray while the patient was inhaling through the mouth were:

1st dose 0.003 ml (as aerosol)
2nd dose 0.009 ml (as aerosol)
3rd dose 0.015 ml (as aerosol)

The patients forced expiratory flow rates (FEV1) were measured by spirometry after each dose. No broncho-constricting effects resulted. The substances present in "antiallergenic agent" are thought not likely to produce bronchoconstriction. In any case they would be inhaled in a treated house (if at all) in such high dose as we have used in the tests.

IV EFFECTIVENESS OF ANTI ALLERGIC AGENT IN THE FIELD

The solution known as "anti-allergenic agent" has been found to both kill house dust mites and remove their allergenic properties under laboratory conditions. The following is aimed at testing the effectiveness of the solution in the field, that is, to determine whether or not the symptoms of an allergy sufferer improve after a controlled part of his environment, namely his home, is treated with the solution.

Two preliminary studies have been made of two asthmatic patients.

Forced expiratory flow rates (an index of airways resistance and asthma) were measured four times daily for periods before and after the patients houses had been treated with antiallergenic agent. Carpets, curtains, other fabrics and floors were sprayed or mopped with the antiallergenic solution. Average percentage improvement in respiratory airflow after house treatment is shown in Table IV.

TABLE IV

| | EXPIRATORY FLOW RATE | | PERCENT IMPROVEMENT |
| --- | --- | --- | --- |
| | BEFORE HOUSE TREATED WITH ANTIALLERGENIC AGENT | AFTER HOUSE TREATED WITH ANTIALLERGENIC AGENT | |
| Patient 1 | *136 (av. over 6 weeks) | 160 (av. over 5 weeks) | 17.6% |
| Patient 2 | 532 (av. for 1 week) | 580 (av. over 3 weeks) | 9.0% |

*The flow rates for the two patients were measured on instruments with different arbitrary scales and therefore are not directly comparable. However, the percentage improvement in each patient is comparable.

I claim:

1. A method of removing allergens from an environment which comprises treating said environment with an antiallergenically effective amount of tannic acid in conjunction with a miticidally effective amount of miticide such as to remove said allergens from said environment, wherrein the allergens are selected from the group consisting of house dust mite allergens selected from the group consisting of *D. farinae* and *D. Pteronyssinus*.

2. A method according to claim 1, wherein the environment comprises air.

3. A method according to claim 1, wherein said tannic acid is contained in an amount of 0.1 to 10 weight %.

4. A method according to claim 1, wherein the miticide is selected from the group consisting of conventional insecticides and alcohols.

5. A method according to claim 4, wherein the insecticide is selected from the group consisting of pyrethrins, pyrethroids and organophosphorous compounds.

6. A method according to claim 5, wherein the tannic acid is in a 0.5 to 5% w/v solution in a solvent comprising
   ethanol 20 to 40% v/v
   water 50 to 70% v/v
   benzyl alcohol 5 to 20% v/v.

7. A method according to claim 6, wherein 1% v/v tannic acid is in a solvent comprising
   30% v/v ethanol
   60% v/v water and
   10% v/v/benzyl alcohol.

8. A method according to claim 4, wherein the alcohol is selected from the group consisting of ethanol and benzyl alcohol.

9. A method according to claim 4, wherein the alcohol is benzyl alcohol.

10. An aqueous composition adapted for removal of allergens from an environment, said allergens being house dust mite allergens selected from the group consisting of *D. farinae* and D. Pteronyssinus, which comprises an admixture of the following components:
    (a) 0.1 to 10 weight % tannic acid,
    (b) a miticidally effective amount of benzyl alcohol and,
    (c) an environmentally acceptable aqueous carrier.

11. A composition according to claim 10 which comprises a 0.5 to 5% w/v solution of tannic acid in a solvent comprising
    ethanol 20 to 40% v/v
    water 50 to 70% v/v and
    benzyl alcohol 5 to 20% v/v.

12. A composition according to claim 11 comprising
    30% v/v ethanol
    60% v/v water
    10% v/v benzyl alcohol and
    1% v/v tannic acid.

* * * * *

UNITED STATES PATENT AND TRADEMARK OFFICE
CERTIFICATE OF CORRECTION

PATENT NO. : 4,806,526
DATED : February 21, 1989
INVENTOR(S) : Wesley F. Green

It is certified that error appears in the above-identified patent and that said Letters Patent is hereby corrected as shown below:

Col. 2, line 18      Delete "0.20-40%" and substitute --20-40%--

Col. 2, line 19      Delete "0.50-70%" and substitute --50-70%--

Col. 2, line 20      Delete "0.5-20%" and substitute --5-20%--

Col. 3, line 66      Delete "(phlem)" and substitute --(phleum)--

Col. 5, Table III, Experiment No. 8, last column      Delete "01" and substitute --04--

Col. 7, line 22      Correct spelling of --wherein--

Signed and Sealed this

Twelfth Day of December, 1989

Attest:

JEFFREY M. SAMUELS

Attesting Officer      Acting Commissioner of Patents and Trademarks